United States Patent
Polster

(10) Patent No.: US 9,381,035 B2
(45) Date of Patent: Jul. 5, 2016

(54) PERCUTANEOUS NEEDLE GUIDE AND METHOD

(71) Applicant: THE CLEVELAND CLINIC FOUNDATION, Cleveland, OH (US)

(72) Inventor: Joshua M. Polster, Shaker Hts., OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 181 days.

(21) Appl. No.: 14/197,462

(22) Filed: Mar. 5, 2014

(65) Prior Publication Data

US 2014/0257319 A1 Sep. 11, 2014

Related U.S. Application Data

(60) Provisional application No. 61/774,242, filed on Mar. 7, 2013.

(51) Int. Cl.
*A61B 19/00* (2006.01)
*A61B 17/34* (2006.01)

(52) U.S. Cl.
CPC ..... *A61B 17/3403* (2013.01); *A61B 2017/3407* (2013.01); *A61B 2090/068* (2016.02)

(58) Field of Classification Search
CPC ............... A61B 19/201; A61B 2017/3407; A61B 2019/467; A61B 2019/468; A61B 17/3403; A61B 2017/3405; A61B 8/0841
USPC ................................................ 606/130
See application file for complete search history.

(56) References Cited

U.S. PATENT DOCUMENTS

| 6,217,596 B1 * | 4/2001 | Farah ............. A61F 9/0136 606/166 |
| 2004/0243146 A1 | 12/2004 | Chesbrough et al. |
| 2006/0229641 A1 | 10/2006 | Gupta et al. |
| 2007/0149878 A1 | 6/2007 | Hankins |

* cited by examiner

*Primary Examiner* — Katherine M Shi
(74) *Attorney, Agent, or Firm* — Tarolli, Sundheim, Covell & Tummino LLP

(57) ABSTRACT

A percutaneous needle guide includes a housing and an inclinometer secured to the housing for sensing a two dimensional inclination of the housing relative to the earth's gravitational field and for providing an indication thereof. A percutaneous needle is slidably mounting to the housing in a fixed axial orientation relative to the housing. A needle measuring device is mounted in the housing and operative by linear motion of the percutaneous needle so as to measure the linear position of the percutaneous needle relative to the housing and providing a measurement indication.

8 Claims, 3 Drawing Sheets

PERCUTANEOUS NEEDLE GUIDE AND METHOD

RELATED APPLICATION

This application claims priority from U.S. Provisional Application No. 61/774,242, filed 7 Mar. 2013, the subject matter of which is incorporated herein by reference in its entirety.

FIELD OF THE INVENTION

The present invention is directed to a percutaneous needle guide and method for use in image guided procedures.

BACKGROUND

Cross-sectional imaging for guiding percutaneous procedures in the human body is known. Such procedures use direct visualization to determine a safe needle path that hopefully avoids arteries, veins, nerves, bowel, etc. These known procedures include a planning phase in which scout images are obtained to identify a target such as a lesion. Next, as part of the planning phase, a safe path to the lesion is determined including identification of a skin entrance site. The length of the needle required to reach the target along the selected path is determined. After this planning phase, the procedure is carried out. As part of the procedure, the needle is inserted into the skin at an approximate angle determined during the planning phase but only to a minimal or shallow depth. The patient is then moved into an examination gantry of an imaging device such as CT scanner. While in the scanner, images are obtained that identify the actual position of the needle relative to the target and the planned path. The patient is then pulled out from the scanner and the needle is repositioned and inserted deeper. This process is repeated until the target is reached.

SUMMARY OF THE INVENTION

In accordance with one example embodiment of the present invention a percutaneous needle guide includes a housing and an inclinometer secured to the housing for sensing a two dimensional inclination of a reference surface of the housing relative to the earth's gravitational field and for providing an indication thereof. A percutaneous needle is slidably mounted to the housing in a fixed axial orientation relative to the reference surface of the housing. A needle measuring device is mounted in the housing and operative by linear motion of the percutaneous needle to measure the linear position of the percutaneous needle relative to the reference surface of the housing and providing a measurement indication.

In accordance with another example embodiment of the present invention, a method is provided for guiding a percutaneous needle comprising the steps of placing the percutaneous needle into a housing, sensing a two dimensional inclination of the housing relative to the earth's gravitational field and providing an indication thereof, slidably mounting a percutaneous needle to the housing in a fixed axial orientation relative to the housing, and measuring the linear motion of the percutaneous needle relative to the housing and providing a measurement indication.

BRIEF DESCRIPTION OF THE DRAWINGS

The foregoing and other features and advantages of the present invention will become apparent to those skilled in the art to which the present invention relates upon reading the following description with reference to the accompanying drawings, in which.

DETAILED DESCRIPTION

Figure 1:
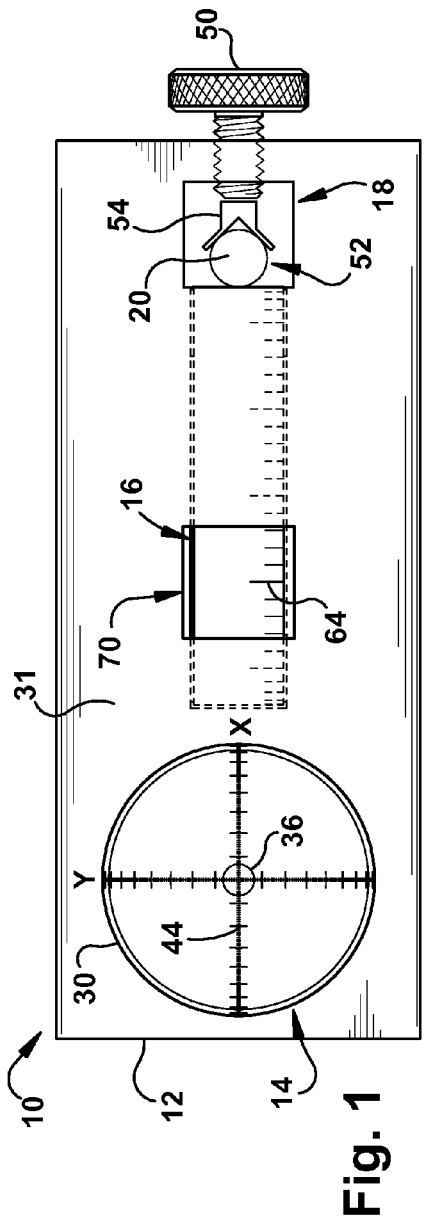
FIG. 1 is a top view of a percutaneous needle guide made in accordance with an example embodiment of the present invention.
Figure 2:
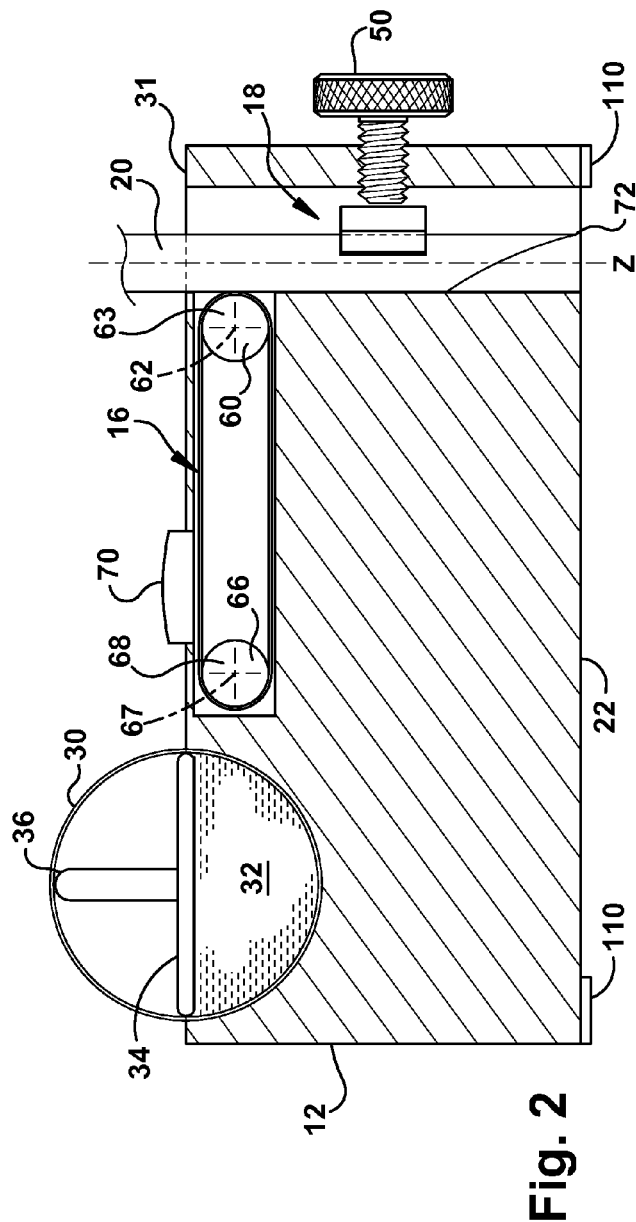
FIG. 2 is a side elevational cross-sectional view of the percutaneous needle guide of FIG. 1.

Referring to FIGS. 1 and 2, a percutaneous needle guide 10, made in accordance with an example embodiment of the present invention, is shown. The guide 10 includes a housing 12 having an inclinometer 14, a linear needle measuring device 16, and an adjustable needle holding device 18. A percutaneous needle 20 is slidably received in the adjustable needle holding device 18 and is operatively coupled to the linear needle measuring device 16. The adjustable needle holding device 18 is adapted to slidably hold any of a plurality of different diameter percutaneous needles along a Z-axis that is perpendicular to a bottom wall 22 of the housing 12. The bottom wall 22 of the housing 12 is used as a reference surface for further measurements.

The inclinometer 14, which may also be referred to as a clinometer or a level sensor, can take any of several known forms. The inclinometer 14 measures the inclination of the housing 12 relative to the earth's gravitational field, and specifically, the position of the reference surface 22 relative to the earth's gravitational field.

In accordance with one example embodiment of the present invention, the inclinometer 14 could include a vessel 30 mounted in a top wall 31 of the housing 12. The surface of the top wall 31 is parallel to the bottom wall 22. Those skilled in the art will appreciate, that for the purposes of the inclinometer 14, the surface of the top wall 31 is, in effect, also a reference surface.

The vessel 30 is, in accordance with one example embodiment of the present invention, generally circular shape, and includes a liquid 32 and a float 34. The float 34 includes a centrally positioned indicator portion 36 that extends upward from the float. When the housing 12 has its bottom reference wall 22 perpendicular to the earth's gravitational field, the indicator portion 36 is centered at the top of the vessel 30. This is referred to as the zero angle position, i.e., no inclination of the housing 12.

The vessel 30 includes angle indication markings 44 along an X-axis direction and a Y-axis direction so that the position of the indicator portion 36 relative to the markings 44 will provide an indication of the angle of inclination of the housing 12 relative to the earth's gravitational field. Values along the X-axis represent pitch and values along the Y-axis represents roll of the housing 12 relative to the earth's gravitational field.

The device 18 includes an adjustable screw 50 threaded into the housing 12 and into a needle receiving passage 52 of the housing 12. A V-shaped needle holder 54 is slidably mounted in the passage 52 and receives the needle 20 positioned in the passage 52 and slidably holds the needle 20 so that its axis is parallel with the Z-axis of the housing 12. A linear measuring device 16 includes a first wheel 60 mounted for rotation about an axis 62 via an axle 63. The first wheel 60 is positioned to contact the needle 20 when the screw 50 is turned so as to snug the V-shaped needle holder 54 against the needle 20. The V-shaped holder 54 has a bearing surface that allows the needle 20 to slide along the Z-axis.

When the needle 20 is slid in the housing in a Z-axis direction, the linear movement of the needle 20 causes the first wheel 60 to rotate about the axis 62. A measurement tape 64 wraps around the first wheel 60 and a second wheel 66 mounted for rotation about an axis 67 on an axle 68 mounted substantially in parallel to the axis 62. A measurement viewing window 70 is located in the housing 12 above the measuring tape 64 that allows the user to view a linear position measurement of the needle 20. The position indication provided by the measurement tape can be calibrated so that a zero position indication can be provided through the window 70 when the needle tip 72 is positioned even with the bottom wall 22 of the housing. This is accomplished by sliding the needle 20 until a zero measurement is indicated in the window 70, loosening the adjustment screw 50 until the needle 20 no longer contacts the measurement tape, slide the needle until the tip 72 is flush with the bottom wall surface 22, then re-tightening the adjustment screw. The length of tape needed and the number of internal wheels need can be adjusted so as to permit sufficient linear measurement of needle movement to a selected Z-axis depth.

Figure 4:
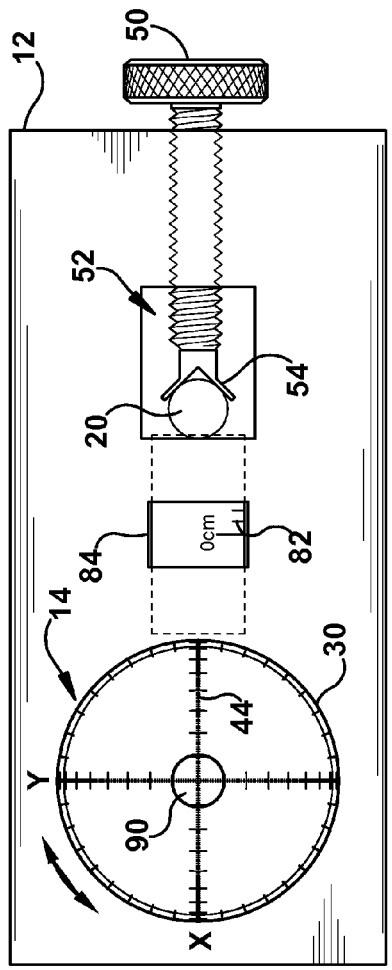
FIG. 4 is a top view of a percutaneous needle guide made in accordance with another example embodiment of the present invention.
Figure 5:
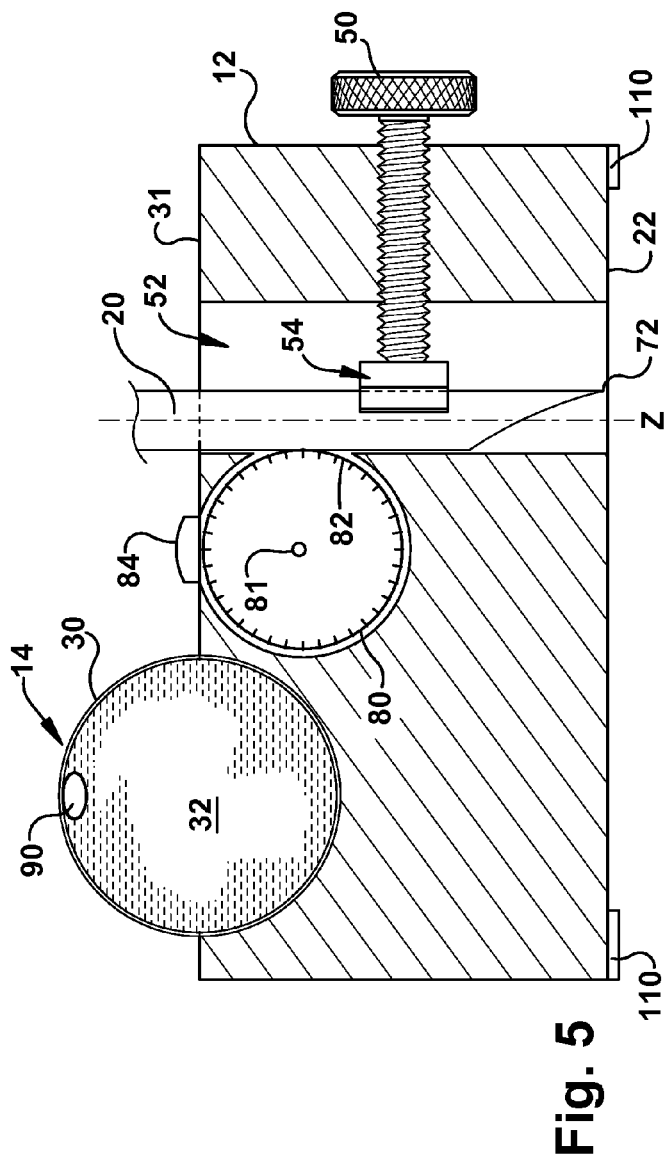
FIG. 5 is a side elevational cross-sectional view of the percutaneous needle guide of FIG. 4.

Referring to FIGS. 4 and 5, another example embodiment of a measuring device is illustrated including a single measurement wheel 80 operatively contacting the needle 20 and mounted for rotation about an axis 81. The single wheel 80 includes measurement indications 82. The wheel is mounted below a clear measurement window 84 for providing a measurement indication of linear needle position along the Z-axis. The combination of the measurement wheel 80 and needle 20 can be calibrated in a similar manner as with the measurement tape.

Also, the vessel 30 could be filled with a supermajority of liquid except for a relatively small area of gas that forms a bubble 90 that would float and provide an indication of the inclination of the housing 12. Furthermore, the vessel 30 could be mounted in the housing 12 so that it could rotate about the Z-axis of the housing 12 so that the angle indications could be rotated to any desired angle relative to an X and Y axis of the housing itself. Such an arrangement provides a different zero position option and angle reading option.

Figure 3:
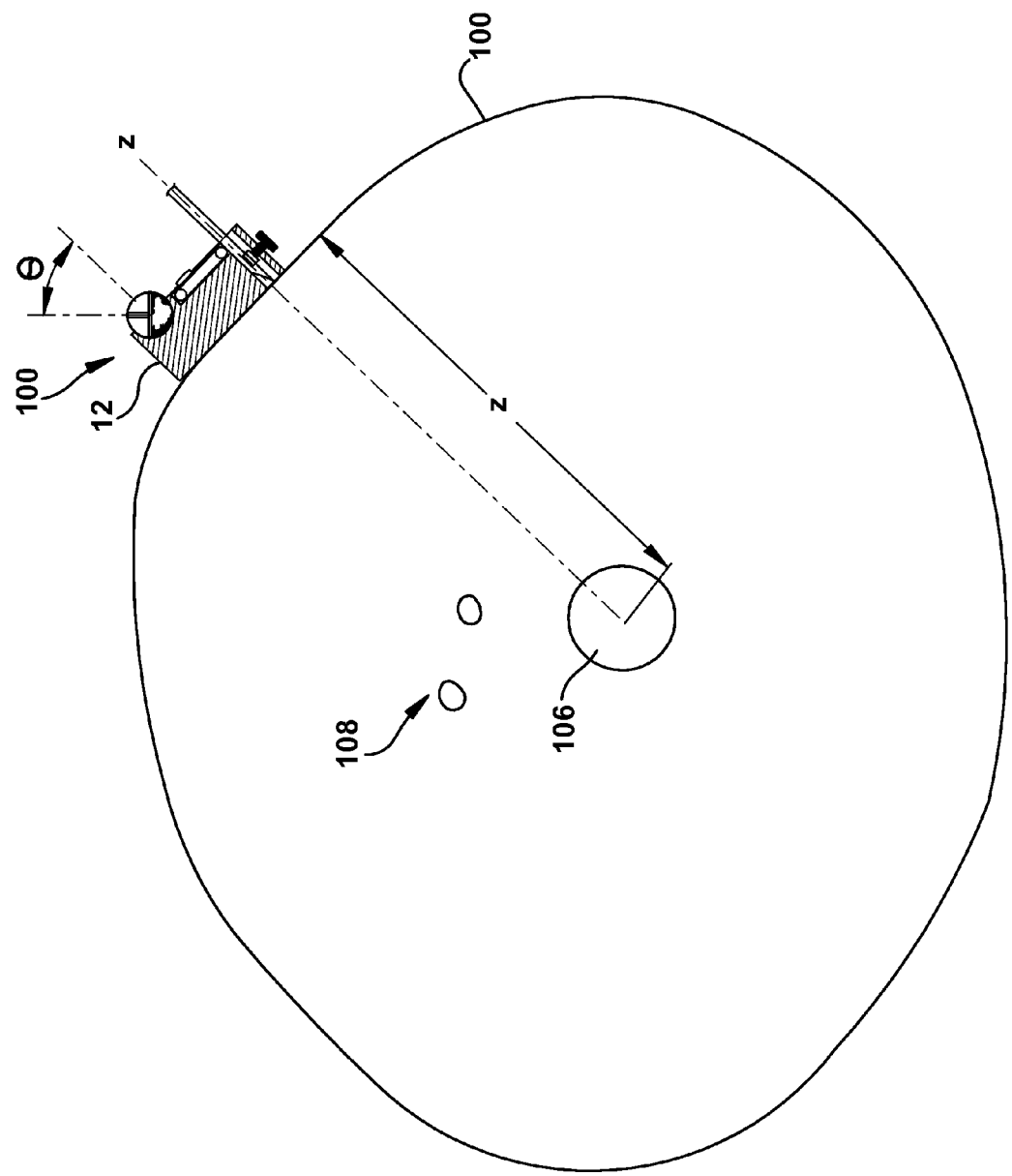
FIG. 3 is an illustration of the percutaneous needle guide of FIG. 1 operatively placed on a patient viewing the patient in cross-section.

Referring to FIG. 3, an example use of the percutaneous needle guide 10 of the present invention on a patient 100 (shown in cross-section) is illustrated. Assume that the patient 100 has a lesion 106 and nearby blood vessels 108. Further, assume that it is desired to biopsy the lesion using a percutaneous needle. It is desirable to have the needle enter the lesion 106 and not hit the blood vessels 108. The patient 100 is first placed into an imaging gantry such as a CT scanner. Images are obtained to identify the actual position of the lesion and blood vessels. The X, Y angle θ is determined and the Z axis depth is determined along a best path scenario to hit the target. The guide 10 is positioned onto the patient at the determined X, Y angle and the needle inserted to the determined depth along the Z axis using the guide measuring device. The inclination reading of the guide 10 and the Z axis depth measurement are visible to the doctor so that the needle insertion could occur while the patient is in the gantry. Also, the variable needle holding arrangement permits all needle sizes needed.

Referring to FIG. 2, adhesive mounting devices 110 could be attached to the bottom wall 22 of the housing 12 to aid in securing the housing 12 to the patient 100 during any procedure. In accordance with one embodiment, the adhesive feet 110 could be malleable flaps or other means for allowing the device 10 to adhere to the skin surface of the patient without requiring the device 10 to rest flush with the skin surface.

In accordance with one example embodiment, the guide 10 is made of plastic with liquid in the inclinometer 14. If the guide 10 is to be used with imaging devices other than CT scanners or MRI scanners, then the guide 10 could be made with metal parts. For example, if the guide were to be used in a biopsy procedure using ultrasound guidance, the guide could have metal parts. Also, under such uses, the inclinometer could be an electronic inclinometer instead of the float arrangement described. Also, an electronic needle displacement measuring device could also be used in situations where metal is not a concern. Using an electronic inclinometer and an electronic needle displacement measuring device permits use of a computer for monitoring and feedback of the sensor signals.

From the above description of the invention, those skilled in the art will perceive improvements, changes and modifications. For example, the adjustable needle holding device 18 could be a different type of slidable securing means such as a tape, string, or plastic strap that fits into a groove in the housing 12 between the needle and the housing. Once the needle is placed into the needle receiving passage 52, the plastic strap is fed through the groove to take up the space between the needle and the housing or the "V" shaped member to hold the needle in operative contact with the measuring tape or wheel. Also, rather than an inclinometer that uses fluid floats or bubbles, a weighted needle arrangement could be used with one needle for the X-axis and one needle for the Y-axis. Each X, Y needle would pivot about its associated mounting axle with the weighted end below the pivot point. Such improvements, changes and modifications within the skill of the art are intended to be covered by the appended claims.

Having described the invention, the following is claimed:

1. A percutaneous needle guide comprising;
    a housing, wherein the housing includes a bottom wall;
    an inclinometer secured to the housing for sensing a two dimensional inclination of the housing relative to the earth's gravitational field and for providing an indication thereof;
    a slidable percutaneous needle mounting arrangement secured to the housing for slidably holding a percutaneous needle in a fixed axial orientation relative to the housing, wherein the slidable percutaneous needle mounting arrangement is configured to slidably hold any of a plurality of different diameter percutaneous needles along a Z-axis that is perpendicular to the bottom wall of the housing; and
    a needle measuring device mounted in the housing and operative with linear motion of the percutaneous needle so as to measure the position of the percutaneous needle relative to the housing and providing a measurement, the needle measuring device including a first wheel mounted on a wheel axis, the first wheel being positioned to contact the needle when the needle holder is slidably held against the needle, and the needle measuring device includes a measurement tape positioned laterally between the first wheel and the needle, the measurement tape being configured to wrap around at least a portion of a circumference of the first wheel;

wherein linear movement of the needle substantially parallel to the Z-axis causes the first wheel to rotate about the wheel axis and facilitate movement of the measurement tape proportional to linear movement of the needle.

2. The percutaneous needle guide of claim 1, wherein the needle receiving passage is perpendicular to the bottom wall of the housing, and wherein a needle holder is slidably mounted in the passage, receives the needle positioned in the passage, and slidably holds the needle with a longitudinal axis of the needle being parallel with the Z-axis of the housing.

3. The percutaneous needle guide of claim 1, including a measurement viewing window located in the housing to permit viewing of a position of the measuring tape from outside the housing, the position of the measuring tape with respect to the housing indicating a linear position of the needle relative to the housing.

4. The percutaneous needle guide of claim 1, wherein the housing includes a top wall and the inclinometer includes a vessel mounted in the top wall of the housing, the vessel including a liquid.

5. The percutaneous needle guide of claim 4, wherein the vessel includes a float, the float including a centrally positioned indicator portion that extends upward from the float such that placement of the top wall of the housing perpendicular to the earth's gravitational field causes centering of the indicator portion at the top of the vessel;
 wherein the vessel includes at least one angle indication marking along an X-axis direction and at least one angle indication marking along a Y-axis direction, the angle indication markings configured to provide an indication of the angle of inclination of the housing relative to the earth's gravitational field responsive to a position of the indicator portion relative to the angle indicator markings.

6. The percutaneous needle guide of claim 4, wherein the vessel is filled with a supermajority of liquid and with a superminority of gas which forms an indicator bubble, the indicator bubble being lighter than the remaining liquid in the vessel such that that placement of the top wall of the housing perpendicular to the earth's gravitational field causes centering of the indicator bubble at the top of the vessel.

7. The percutaneous needle guide of claim 4, wherein the vessel is rotatably, about the Z-axis, mounted in the housing to permit angle indication markings of the vessel to be rotated to any desired angle relative to X and Y axes of the housing to provide options for zero position and angle reading for the inclinometer.

8. The percutaneous needle guide of claim 1, wherein the needle measuring device includes a measurement wheel operatively contacting the needle and mounted for rotation about an axis, the measurement wheel being positioned to contact the needle when the needle holder is slidably held against the needle, the measurement wheel including at least one measurement indication and being mounted in a predetermined relationship to a measurement window in the housing;
 wherein linear movement of the needle substantially parallel to the Z-axis causes the measurement wheel to rotate about the wheel axis proportional to linear movement of the needle and provide a measurement indication, viewable from outside the housing through the measurement window, of linear needle position along the Z-axis.

\* \* \* \* \*